United States Patent [19]

Casper

[11] Patent Number: 4,521,187

[45] Date of Patent: Jun. 4, 1985

[54] DENTAL ANALYZER

[76] Inventor: James A. Casper, 1830 S. 8th Ave., Yuma, Ariz. 85364

[21] Appl. No.: 621,245

[22] Filed: Jun. 15, 1984

Related U.S. Application Data

[63] Continuation-in-part of Ser. No. 469,399, Feb. 24, 1983, Pat. No. 4,460,339.

[51] Int. Cl.³ .............................................. A61C 9/00
[52] U.S. Cl. ...................................................... 433/72
[58] Field of Search ...................... 433/54, 55, 56, 72, 433/73, 214; 33/174 D, 174 PA, 175

[56] References Cited

U.S. PATENT DOCUMENTS

| | | | |
|---|---|---|---|
| 1,753,965 | 4/1930 | Ralph | 33/174 D |
| 2,014,289 | 9/1935 | Page | 433/72 |
| 3,321,832 | 5/1967 | Weisberg | 433/214 |
| 3,896,551 | 7/1975 | Stuart | 433/214 |
| 4,182,312 | 1/1980 | Mushahac | 433/214 |

Primary Examiner—Robert Peshock
Attorney, Agent, or Firm—Clarence A. O'Brien; Harvey B. Jacobson

[57] ABSTRACT

A denture analyzing instrument gauges landmark points established on existing dentures to record geometrical data associated therewith for transfer to replacement dentures assembled on models spaced from each other by a template conforming to the recorded data and serving as a guide for assembling the replacement dentures.

9 Claims, 8 Drawing Figures

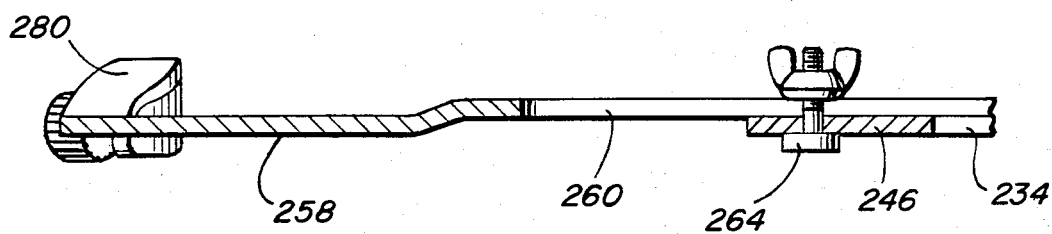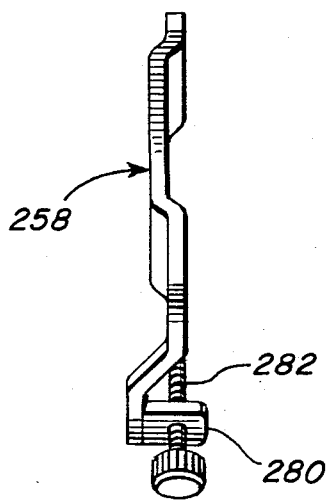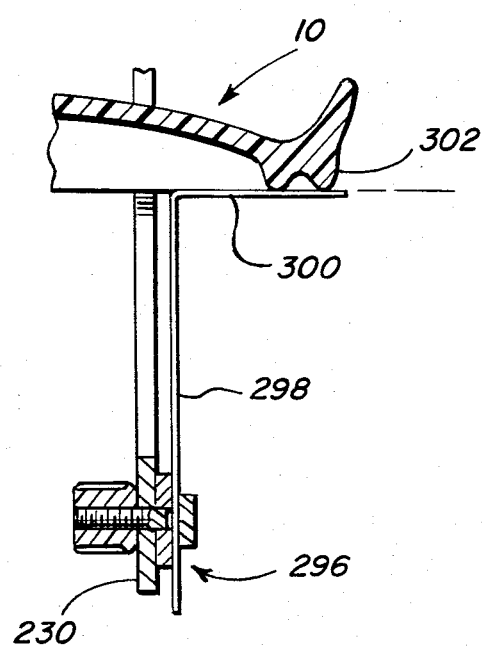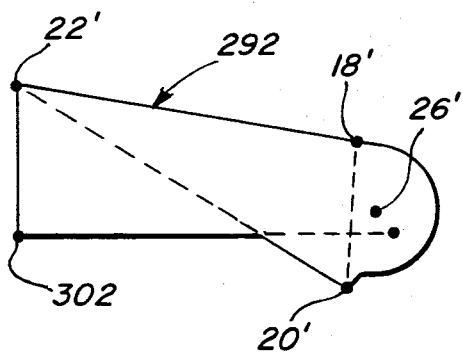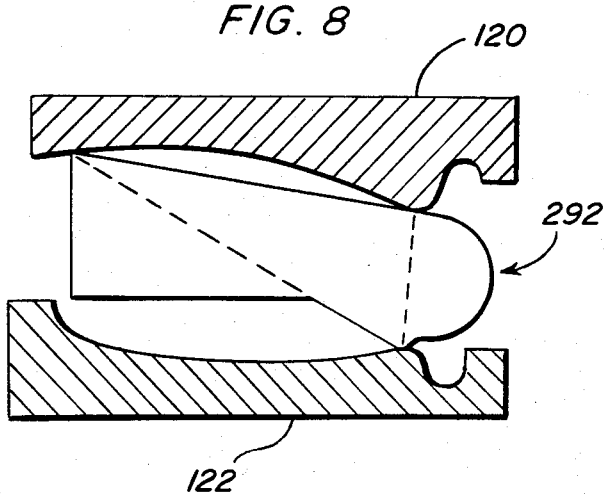

DENTAL ANALYZER

BACKGROUND OF THE INVENTION

This invention relates to a method and apparatus useful in the making of artificial dentures as replacements for old or existing dentures, and is an improvement over the invention disclosed in my prior copending application, Ser. No. 469,399, filed Feb. 24, 1983 now U.S. Pat. No. 4,460,339 issued July 17, 1984, with respect to which the present application is a continuation-in-part.

Gauging instruments for measuring various geometrical relationships associated with dental prosthesis and human dental anatomy are disclosed in my prior copending application for utilizing experience gained from the immediate past use of existing dentures by a patient as guidance for the fabrication of replacement dentures for the same patient.

It is an important object of the present invention to provide an improved instrument through which the vertical dimensions for fabrication of dental prosthesis are gauged in an efficient and accurate manner.

SUMMARY OF THE INVENTION

In my prior copending application, the disclosure of which is hereby incorporated by reference, a method and apparatus is disclosed whereby a removable type of dental prosthesis may be remade or replaced with one to which desirable geometrical features are transferred with or without modification. Toward that end, upper and lower dentures while fitted within the patient's oral cavity are adhesively fixed to each other in occlusal relation and then removed from the patient. A plurality of reference points are then established on the interfixed dentures. A denture analyzing instrument is then aligned with the median plane and adjusted for contact with the points lying in the median plane in order to measure the geometrical relationships defined by such points. The measurements made by the denture analyzing instrument with respect to the median plane are recorded on paper or the like from which a jaw spacing template is made. Models of the upper and lower jaws are then cast and the same reference points located thereon. The template aforementioned is utilized to hold the models in spaced relation to each other reproducing to occlusal or biting positions associated with the old existing dentures. Building or replacement dentures may then be initiated by assembly on such models. Geometrical data recorded by use of the denture analyzing instrument may also be utilized to assemble artificial teeth in proper orientation onto the denture base plate. Adjustment of the denture analyzing instrument while aligned with the median plane is facilitated by non-pivotal clamping thereof to the upper denture adjacent the distal border at closely spaced points of contacts. Additional pointer assemblies are utilized to gauge the posterior occlusal plane by contact with a molar tooth on the upper denture and to indicate the patient's ala-tragus line in relation to the denture being replaced.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 4 is an enlarged partial section view taken substantially through a plane indicated by section line 4—4 in FIG. 2.

FIG. 5 is a partial end view of the instrument shown in FIG. 2.

FIG. 6 is an enlarged partial section view taken substantially through a plane indicated by section line 6—6 in FIG. 2.

FIG. 7 is a side elevation view of a template on which geometrical relationships are recorded by use of the dental analyzing instrument illustrated in FIGS. 2–6.

FIG. 8 is a section view in the median plane through upper and lower jaw models held in spaced relationships to each other by the template.

DETAILED DESCRIPTION OF PREFERRED EMBODIMENT

Figure 1:
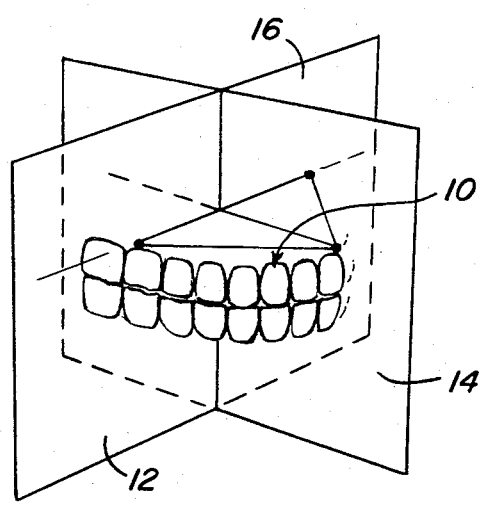
FIG. 1 is a perspective view showing interfixed upper and lower dentures intersected by perpendicular median and frontal planes.

Referring now to the drawings in detail, FIG. 1 illustrates full upper and lower dentures 10 and 12 which have been adhesively interfixed by a sticky wax in occlusal condition while fitted within a patient's mouth. The upper and lower dentures represent an existing or old dental prosthesis which is to be remade or replaced in accordance with the present invention. Also represented in FIG. 1 is a median plane 14 which extends centrally through the incisor portion of the dentures perpendicular to an intersecting frontal plane 16 which extends through the molar portions of the dentures. The interfixing of the upper and lower dentures is accomplished while the molar portions of the dentures are in biting contact at contact points defining an occlusal plane, as is well known in the art.

Figure 2:
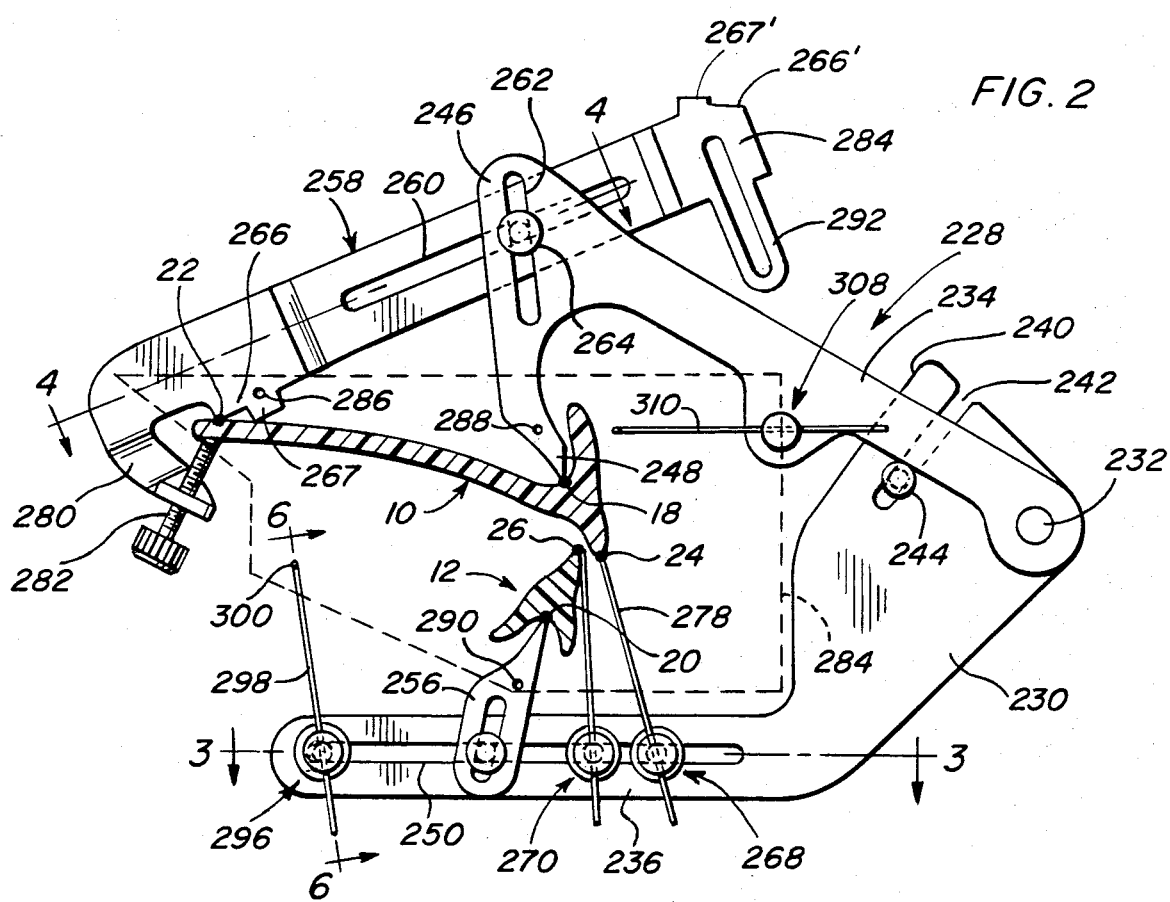
FIG. 2 is a section view through interfixed upper and lower dentures in the median plane being measured by a denture analyzing instrument shown in side elevation.

FIG. 2 illustrates a median plane section through the interfixed upper and lower dentures 10 and 12. In accordance with the present invention, various reference locations are established by marking or the like on the tissue contacting surfaces of the dentures. These reference locations include anatomical landmarks such as the incisive papilla depression at point 18, the crest of the lower anterior ridge at point 20 and the fovea palatina at point 22. Alternatively, reference point 22 may be located on the vibrating line between the hard and soft portions of the upper palate. In cases where fovea palatina or vibrating line is indistinct or unreliable for location of the reference point 22, an arbitrary location in the median plane is utilized since it is necessary to precisely locate only point 18 in the median plane at the most reliable incisive papilla landmark. An additional point 24 on the upper denture 10 is located at its incisal or biting edge of the upper central incisor while a point 26 is established on the lower denture 12 at its incisal edge on the lower central incisor.

With continued reference to FIG. 2, a generally planar dental analyzing instrument 228 is shown in engagement with the upper denture 10 at the reference points 18 and 22 and the lower denture 12 at point 20 in order to measure or gauge the geometrical relationships associated therewith. The instrument 228 includes a base 230 adapted to be aligned with the median plane as shown in FIG. 2. A pivot member 232 pivotally interconnects the base at a pivot axis with an elongated pivot arm 234. The pivot arm extends from the pivot member 232 over one lateral face of the base for angular displacement in sliding contact therewith. The base has an elongated arm portion 236.

The pivot arm 234 projects radially from an edge 240 of the base having a straight slot 242 formed therein. The slot 242 slidably mounts a stop element 244 that is releasably locked in an adjusted position by means of a wing nut. The pivot arm 234 is engageable with the stop element 244 as shown so as to limit its angular displacement in one direction. The pivot arm has an enlarged end portion 246 opposite the end portion through which the pivot 232 extends. A fixed tip portion 248 of the pivotal arm projects from the enlarged end portion 246 and is adapted to be received within the incisive papilla depression for contact with the upper denture at landmark point 18.

The elongated portion 230 of the base is provided with a slot 250. An adjustably positioned tip member 256 projects from elongated portion 230 for contact with the lower denture 12 at point 20 as shown in FIG. 2.

The third reference point 22 in the median plane 14 is gauged by an adjustable contact element 258 as shown in FIG. 2. The element 258 is accordingly provided with a slot 260 intersecting a slot 262 in the enlarged end portion 246 of the pivot arm. A wing nut lock 264 extends through the intersection of the slots 260 and 262 in order to releasably lock the element 258 in an angular and longitudinal adjusted position relative to the pivot arm 234. One longitudinal offset end portion of the element 258 is provided with a contacting edge 266 shown engaging the upper denture at reference point 22 in FIG. 2. A formation 267 projects from the lower edge of the element 258 adjacent to edge 266 for abutment with denture 10 adjacent to point 22. Pivoting of the instrument relative to denture 10 is thereby prevented when clamped thereto by a screw 282 threadedly mounted on a curved formation 280 at the end of element 258. The clamping screw engages the underside of denture 10 at the center of the distal border as shown in FIG. 2, forwardly of any post-dam. The longitudinal end portion 284 of element 258 opposite end formation 280 is also offset and provided with a contact edge 266' and a projection 267' similar to contact edge 266 and projection 267. A slotted projection 292 extends laterally from element 258 adjacent the end opposite formation 280 in order to accommodate future attachment of the instrument to a bite recording device.

Figure 3:
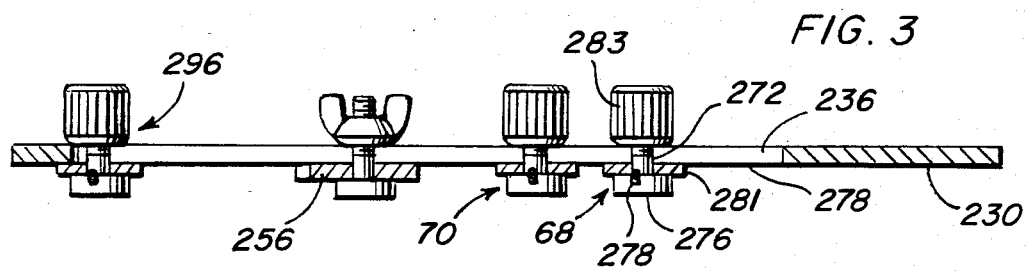
FIG. 3 is a longitudinal section view taken substantially through a plane indicated by section line 3—3 in FIG. 2.

With reference to FIGS. 2 and 3, a pair of angular pointer assemblies 268 and 270 are mounted on the elongated portion 236 of the base. Each of the pointer assemblies includes a threaded stem 272 extending through slot 250. A flat head 276 is connected to one end of the stem 272 abutting a wire pointer element 278 which extends through an aperture formed in the stem. The wire element is thereby sandwiched between the head 276 and a washer 281 abutting the side face of the extensible arm. A thumb nut 283 is threaded onto the stem at the end opposite the head 276 for locking engagement with the base. Thus, each of the wire elements 278 associated with the adjustable pointer assemblies 268 and 270 may be adjusted along the longitudinal axis of base portion 236, longitudinally adjusted along its own wire axis and angularly adjusted before being locked in position with the ends of the wire elements contacting the upper and lower dentures at points 24 and 26. The adjusted angular positions of the wire elements 278 provide incisor position and angle guidance as will be explained hereinafter.

With the instrument 228 locked in its adjusted gauging condition as shown in FIG. 2, the pivot arm 234 may be pivotally displaced upwardly from its position engaging the stop 244 so that the instrument may be withdrawn from the interfixed dentures 10 and 12 without disturbing its gauging condition. Once withdrawn from the dentures, the pivot arm of the instrument is returned to the adjusted position engaging stop 244 and then placed on a sheet of paper or recording material backed by a wood block 284 as shown by dotted line in FIG. 2 to which the instrument may be pinned through pinholes 286, 288 and 290 respectively formed in element 258, tip portion 248 of arm 234 and tip member 256. The points gauged by the instrument and recorded may be transferred to a template 292 as shown in FIG. 7 by any suitable marking method to record point 18', 20' and 22' thereon corresponding to the reference points 18, 20 and 22. The additional points 24' and 26' are also recorded on the template. The points 18', 20' and 22' on the template form a spacing triangle.

A pointer assembly 296 similar in construction and adjustment to pointer assemblies 268 and 270 is mounted on base portion 236 to gauge the level of the posterior occlusal plane. This pointer assembly includes a wire element 298 from which a right angle portion 300 extends as more clearly seen in FIG. 6. The pointer assembly is adjusted so that wire portion 300 contacts the occlusal surface of the posterior teeth 302 of upper denture 10 as shown.

Yet another adjustable pointer assembly 308 is mounted on pivot arm 234 intermediate opposite ends thereof as shown in FIG. 2. A wire element 310 is thereby adjusted to record the ala-tragus line drawn on the upper denture 10.

To use the instrument 228, the contact element 258 is initially clamped to the upper denture by the clamping screw 282 to firmly hold contact edge 266 positioned on reference point 22 in the median plane. The wing nut lock 264 is then loosened so that the tip 248 may be brought into contact with the upper denture at point 18 a measured distance from the anterior or posterior border. The stop element 244 is then adjusted so as to abut the pivot arm 234 and tightened. Next, the tip member 256 is adjusted to a position establishing contact with the lower denture 12 at point 20. The incisor pointers 268 and 270 are then set for contact with points 24 and 26, and finally the occlusal plane level pointer 296 is set as aformentioned. The fully adjusted instrument 228 will then be in condition to transfer the vertical dimension data for making of template 292 as shown in FIG. 7. The template not only forms the spacing triangle between points 18', 20' and 22', but also locates the incisor points 24' and 26' and the occlusal plane level point 302'.

FIG. 8 shows upper and lower jaw models 120 and 122 that are cast from the upper and lower impressions taken from the oral cavity of the patient after removal of the old dentures. The upper and lower models 120 and 122 are mounted in an articulator in a manner well known in the art, but spaced from each other by the spacing triangle on template 292. The articulated models are then utilized to assemble a denture being made to replace the old or existing dentures gauged by the instrument 228 as hereinbefore described based on the incisor orientation and occlusal plane level data provided by points 24′, 26′ and 302′ on template 292.

It will be apparent from the foregoing description that the denture analyzing instrument 228 may be utilized for making various median plane measurements furnishing geometrical data associated with old existing dentures including for example, the vertical dimension of occlusion to which the patient has been accustomed, the position and angle of the upper central incisor, the position of the lower central incisor and possibly its estimated angle, the amount of overjet and overbite, anterior incisal guidance from the angular relationship between points 24 and 26, and the anterior ridge relationship of the upper and lower jaws. Also, occlusal plane level information is provided. Permanent records of the foregoing geometrical data may be made from the instrument 228 and the template 292 for mounting upper and lower models in the same relationship as the patient's upper and lower denture bearing areas with respect to the old prosthesis. The template also functions to provide guidance in the fitting of the new upper and lower central incisors at predetermined position and incisal angles for the new prosthesis.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. For use in analyzing reference points in a median plane extending through upper and lower dentures fixed in occlusal relationship to each other, a denture analyzing instrument comprising a planar base adapted to be aligned with said median plane, a pivot mounted on said base, a pivot arm pivotally connected to the base by said pivot, said base having an elongated portion, a contact tip fixed to the pivot arm, adjustable means respectively mounted on the pivot arm and the elongated portion of the base for contact with the dentures at the reference points in the median plane, and means for locking the adjustable means in positions contacting at least two of the reference points while the contact tip contacts a third of the reference points on the upper denture in said median plane, said three of the reference points defining a denture spacing triangle.

2. The instrument as defined in claim 1 wherein one of the adjustable means mounted on the pivot arm comprises an elongated element having a contact portion engageable with the upper denture at one of the reference points, and releasable clamp means engageable with the upper denture in spaced adjacency to said one of the reference points for holding the elongated element in non-pivotal relation to the upper denture.

3. The instrument as defined in claim 2 including an adjustable gauging device mounted on the elongated portion of the base having a wire element adjustably positioned substantially in said median plane and a molar contact element extending from the wire element substantially in a posterior occlusal plane.

4. The instrument as defined in claim 3 including pointer means adjustably mounted on the pivot arm for recording an ala-tragus line drawn on the upper denture.

5. The instrument as defined in claim 1 including an adjustable gauging device mounted on the elongated portion of the base having a wire element adjustably positioned substantially in said median plane and a molar contact element extending from the wire element substantially in a posterior occlusal plane.

6. The instrument as defined in claim 5 including pointer means adjustably mounted on the pivot arm for recording an ala-tragus line drawn on the upper denture.

7. The instrument as defined in claim 2 including pointer means adjustably mounted on the pivot arm for recording an ala-tragus line drawn on the upper denture.

8. The instrument as defined in claim 1 including pointer means adjustably mounted on the pivot arm for recording an ala-tragus line drawn on the upper denture.

9. In an instrument for gauging upper and lower dentures, fixed in occlusal relation to each other, by contact therewith at a plurality of reference points, said instrument having a base, a contact arm pivotally connected to the base, means for locking the arm to the base in an adjusted position engaging the upper denture at one of the reference points and adjustable means mounted on the arm for engaging the upper denture at another of the reference points, the improvement comprising a projection on the adjustable means engageable with the upper denture in spaced adjacency to said other of the reference points, and means for releasably clamping the upper denture to adjustable means at said other of the reference points.

* * * * *